(12) United States Patent
Greiner-Perth

(10) Patent No.: US 12,201,765 B2
(45) Date of Patent: Jan. 21, 2025

(54) NOZZLE UNIT, LIQUID DISPENSER COMPRISING SUCH A NOZZLE UNIT, AND METHODS FOR PRODUCING SUCH NOZZLE UNITS

(71) Applicant: Aptar Radolfzell GmbH, Radolfzell (DE)

(72) Inventor: Jürgen Greiner-Perth, Gottmadingen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 634 days.

(21) Appl. No.: 17/419,911

(22) PCT Filed: Jan. 3, 2019

(86) PCT No.: PCT/EP2019/050115
§ 371 (c)(1),
(2) Date: Jun. 30, 2021

(87) PCT Pub. No.: WO2020/141024
PCT Pub. Date: Jul. 9, 2020

(65) Prior Publication Data
US 2022/0080133 A1    Mar. 17, 2022

(51) Int. Cl.
*A61M 11/00* (2006.01)
*A61M 15/00* (2006.01)
(Continued)

(52) U.S. Cl.
CPC ......... *A61M 11/006* (2014.02); *A61M 11/003* (2014.02); *A61M 15/0021* (2014.02);
(Continued)

(58) Field of Classification Search
CPC .............. A61M 11/006; A61M 11/003; A61M 15/0021; A61M 15/009;
(Continued)

(56) References Cited

U.S. PATENT DOCUMENTS 3,756,472 A * 9/1973 Vos .................... B65D 83/205
                                                              222/189.06
4,014,797 A * 3/1977 Raines .................. A61M 5/165
                                                                      210/457
(Continued)

FOREIGN PATENT DOCUMENTS

CN          1195301 A         10/1998
CN          1964831 A          5/2007
(Continued)

OTHER PUBLICATIONS

Chinese Decision on Rejection issued in corresponding Chinese Application No. 201980087723.0, dated Dec. 22, 2022 (5 pages).
(Continued)

*Primary Examiner* — Bob Zadeh
(74) *Attorney, Agent, or Firm* — FLYNN THIEL, P.C.

(57) ABSTRACT

Two sub-methods are used together to produce a nozzle unit for a liquid dispenser. The methods include adding a nozzle plate into a nozzle channel of a nozzle unit using an assembly tool which elastically expands the nozzle channel. The assembly tool is inserted in the nozzle channel and expands same, thus moving the nozzle plate into its final position where it remains after the assembly tool is removed. The methods also include attaching a filter to a nozzle unit carrier. In a preparation step, a flat filter material is positioned on the end face of the carrier. Only after the filter material is positioned and a connection of the filter material to the end face is established, a separation process is carried out by which the filter material is cut to surround the end face. The filter material positioned on the end face and cut in situ remains.

26 Claims, 11 Drawing Sheets

(51) Int. Cl.
*B05B 15/40* (2018.01)
*B65D 83/14* (2006.01)

(52) U.S. Cl.
CPC .......... *A61M 15/009* (2013.01); *B05B 15/40* (2018.02); *B65D 83/754* (2013.01); *A61M 2202/0468* (2013.01); *A61M 2205/75* (2013.01); *A61M 2207/10* (2013.01)

(58) Field of Classification Search
CPC ...... A61M 2202/0468; A61M 2205/75; A61M 2207/10; A61M 15/0086; B05B 15/40; B05B 1/14; B05B 11/0086; B05B 11/01; B65D 83/754; A24F 40/40; A24F 40/10; B29C 65/02
See application file for complete search history.

(56) References Cited

U.S. PATENT DOCUMENTS

| | | | | |
|---|---|---|---|---|
| 5,279,462 | A * | 1/1994 | Mehoudar | B29C 66/5412 |
| | | | | 239/533.13 |
| 5,497,944 | A * | 3/1996 | Weston | A61M 11/001 |
| | | | | 128/200.22 |
| 5,798,041 | A | 8/1998 | Zuk, Jr. | |
| 7,614,504 | B2 | 11/2009 | South et al. | |
| 7,781,707 | B2 | 8/2010 | Enrietti | |
| 7,892,592 | B1 | 2/2011 | Chen et al. | |
| 9,016,602 | B2 * | 4/2015 | Grether | E03C 1/08 |
| | | | | 239/467 |
| 11,591,780 | B2 * | 2/2023 | Chen | E03C 1/0404 |
| 2006/0081178 | A1 * | 4/2006 | Willey | B05B 5/025 |
| | | | | 118/313 |
| 2012/0012105 | A1 * | 1/2012 | Heskamp | B65D 83/14 |
| | | | | 128/200.23 |
| 2017/0100882 | A1 * | 4/2017 | Saito | B29C 66/12469 |
| 2017/0281880 | A1 * | 10/2017 | Van Egmond | B05B 15/40 |
| 2020/0385201 | A1 * | 12/2020 | Roxhead | B65D 83/7535 |
| 2022/0080133 | A1 * | 3/2022 | Greiner-Perth | B05B 15/40 |

FOREIGN PATENT DOCUMENTS

| | | | | |
|---|---|---|---|---|
| CN | 101184544 | A | 5/2008 | |
| CN | 201933557 | U | 8/2011 | |
| CN | 103334859 | A | 10/2013 | |
| CN | 207238357 | U | 4/2018 | |
| DE | 19622350 | A1 * | 12/1997 | ............ C25D 1/003 |
| EP | 2886185 | A1 | 6/2015 | |
| EP | 2890502 | B1 | 7/2015 | |
| EP | 3275558 | A1 * | 1/2018 | ............ B05B 15/40 |
| FR | 2972995 | A1 | 9/2012 | |
| JP | 2004275941 | A | 10/2004 | |
| KR | 20150111533 | A * | 10/2015 | |
| WO | WO-03106544 | A2 * | 12/2003 | ......... B29C 44/3461 |
| WO | 2015194962 | A1 | 12/2015 | |
| WO | 2018097960 | A1 | 5/2018 | |

OTHER PUBLICATIONS

Chinese Office Action issued in corresponding Chinese Application No. 201980087723.0, dated Apr. 25, 2022 (12 pages).

International Search Report issued in corresponding International Application No. PCT/EP2019/050115 with English translation date of mailing Nov. 5, 2019 (10 pages).

Written Opinion of International Searching Authority issued in corresponding International Application No. PCT/EP2019/050115 dated Nov. 5, 2019 (13 pages).

European Office Action issued in corresponding European Patent Application No. 19 700 633.1 dated Jul. 12, 2024 (7 pages).

* cited by examiner

NOZZLE UNIT, LIQUID DISPENSER COMPRISING SUCH A NOZZLE UNIT, AND METHODS FOR PRODUCING SUCH NOZZLE UNITS

FIELD OF USE AND PRIOR ART

The invention relates to a nozzle unit for a liquid dispenser, and to methods for the production thereof. The invention moreover relates to a liquid dispenser having a nozzle unit of this type which is produced in this way.

A nozzle unit within the meaning of the invention is a structural part of a liquid dispenser located at the end of a liquid path along which the liquid is discharged from a liquid reservoir of the liquid dispenser. Such a nozzle unit is customarily used to generate a spray jet which is then dispensed, for example, into a mouthpiece for the purpose of inhalation.

The nozzle unit is inserted into a housing of the liquid dispenser. The outer surfaces of the nozzle unit that are used for assembly are formed by a plastic carrier. The latter is traversed by a nozzle channel from an inlet side, from which the liquid flows in, to an outlet side, where the dispensing takes place.

A nozzle plate arrangement is usually arranged within the nozzle channel, primarily in the present case a nozzle plate arrangement having a multiplicity of very small nozzle openings through which pressurized liquid is forced. As a result, the liquid is broken up into small or very small droplets, such that, for example, an aerosol is generated that can reach the pharynx or lungs.

The nozzle unit, along with the plastic carrier, not only serves for arranging the nozzle plate arrangement in the flow path, but can also be a carrier for a filter arrangement with which outflowing liquid in front of the nozzle plate arrangement is freed of constituents of the liquid that might block the nozzle openings and thus prevent the proper discharge.

An example of a nozzle unit that is similar in terms of the intended use of the nozzle unit according to the invention is known from WO 2015/194962 A1. The nozzle unit presented in said document has a nozzle plate and various filter surfaces, which are held in a nozzle channel by thermoplastic deformation of the latter.

OBJECT AND SOLUTION

One object of the invention is to make available a nozzle unit of the type in question which has a high degree of reliability as regards the discharge characteristics and which also maintains these over long periods of storage or intensive use. The object of the invention is moreover to make available suitable production methods for this.

According to one aspect of the invention, two methods are proposed for this purpose, which methods are preferably realized jointly and relate to sub-steps of inserting the nozzle arrangement into the nozzle channel and of mounting a filter arrangement on the plastic carrier of the nozzle unit.

In the context of the production of a nozzle unit, the first of the methods serves to insert a nozzle plate arrangement into the metering channel. Corresponding to this, the invention also relates to a nozzle unit having the properties that result from the method.

According to one aspect of the invention, the insertion of the nozzle plate arrangement is carried out using an assembly tool. This assembly tool has an outer contour with an oversize in relation to the nozzle channel, such that the assembly tool, by being introduced into the nozzle channel and applying force there to a nozzle channel wall, can elastically expand the nozzle channel. An end face of the assembly tool is larger than an outer contour of the nozzle plate arrangement.

To insert the nozzle plate arrangement, the plastic carrier is first of all brought into a defined assembly position, preferably with the outlet side of the plastic carrier facing downward. A defined assembly position of this kind can be provided to be absolutely stationary or to be stationary on an assembly carrier that is movable as a whole.

In the stated assembly position, the nozzle plate arrangement is first of all inserted into the nozzle channel from the inlet side and toward the outlet side in a joining direction. For this purpose, the nozzle channel preferably has an inlet-side sub-portion whose cross section is larger than the outer contour of the nozzle plate arrangement, such that the nozzle plate arrangement can be inserted into the nozzle channel without deformation of the latter.

In a particularly simple and preferred configuration, the nozzle plate arrangement can be designed as a one-piece nozzle plate and may have been punched out of a carrier plate by means of a punching operation immediately prior to insertion into the nozzle channel. Here, immediate insertion is understood to mean that punched-out nozzle plates are not first of all brought together in order to be introduced into plastic carriers in a later method step. Instead, according to this preferred procedure, there is just one single handling of punched-out nozzle plate arrangements. The danger of contamination or damage to the nozzle plate arrangement is thus very low. As an alternative to a nozzle plate arrangement composed only of the nozzle plate, the nozzle plate arrangement can additionally have a carrier ring, as will be explained further below.

After the nozzle plate arrangement or, in the case of the simple design, the one-piece nozzle plate has been inserted into the nozzle channel, the assembly tool is then inserted into the nozzle channel in the joining direction from the inlet side, as it were following the nozzle plate arrangement. The stated sequence can also be achieved by first placing the nozzle plate on the end face of the assembly tool and then pushing the assembly tool together with the nozzle plate into the nozzle channel.

As the assembly tool progressively moves into the nozzle channel in the joining direction, the assembly tool increasingly comes into contact with the nozzle channel wall of the nozzle channel and partially elastically expands the latter by means of its outer contour. This expansion allows the nozzle plate arrangement to reach deeper and deeper into the nozzle channel, which is preferably already tapered in the relaxed state, without being damaged in the edge region. As it is increasingly pressed in, the nozzle plate arrangement can come into touching contact with the end face of the assembly tool and can as it were be pushed by the latter. However, such touching contact is not absolutely necessary. Instead, for example, the nozzle plate arrangement can slide deeper and deeper into the nozzle channel solely by means of its weight in the course of the expansion of the nozzle channel, while there is no touching contact, in phases or continuously, between the nozzle plate arrangement and the end face of the assembly tool. In the case of a nozzle plate arrangement with a carrier ring, the assembly tool preferably presses directly against this carrier ring.

When the relative movement between the plastic carrier and the assembly tool ends, the nozzle plate arrangement has reached its end position.

The assembly tool is now withdrawn from the nozzle channel counter to the joining direction. The nozzle plate arrangement remains substantially in its end position; the latter can still change somewhat if the nozzle plate arrangement is also pushed back a little way, counter to the joining direction, under the effect of the resetting of the nozzle channel. The resetting of the nozzle channel upon withdrawal of the assembly tool has the effect that the nozzle plate arrangement is ultimately held by the nozzle channel wall, in particular by two nozzle channel portions on both sides of the nozzle plate, the clearance or open cross section of which after resetting is smaller than the outer contour of the nozzle plate arrangement.

In the region of the nozzle plate arrangement, the latter presses from inside against the resetting wall of the nozzle channel and thus prevents the complete resetting thereof. The nozzle plate arrangement is thus as it were clamped in the nozzle channel. Downstream and upstream from the nozzle plate arrangement, the resetting wall preferably constricts the nozzle channel slightly, such that the nozzle plate arrangement is held with form-fit engagement after removal of the assembly tool.

Although the method can in principle also be used for inserting nozzle plate arrangements into cylindrical nozzle channels, it is advantageous if the nozzle channel tapers in the joining direction, that is to say from the inlet side to the outlet side. Particularly preferably, the nozzle channel has at least one conical sub-portion which, at its end pointing in the direction of the inlet side, preferably has a cross section that is larger than the outer contour of the assembly tool, and which, at its end pointing in the direction of the outlet side, has a cross section that is smaller than the outer contour of the assembly tool.

As the assembly tool is introduced into the nozzle channel, the end face and/or outer contour of the assembly tool comes into contact, in said conical sub-portion, with the nozzle channel wall of the nozzle channel and expands said wall during continued movement. The conical shape leads to an easily reproducible engagement of the nozzle plate arrangement in a region of the nozzle channel that is always progressively widening due to the assembly tool. A preferred opening angle of the conical sub-portion is in the range of between 5° and 15°.

During the progressive insertion of the assembly tool into the nozzle channel in the joining direction, an auxiliary tool can be pushed, in alignment with the assembly tool, into the nozzle channel from the outlet side. This auxiliary tool can be pulled out in particular in the joining direction while the assembly tool is still moving likewise in the joining direction into the nozzle channel.

Depending on the design and movement profile, the auxiliary tool can prevent the nozzle plate from inadvertently moving too far into the nozzle channel. It can additionally help to maintain an exact setting of the end position and/or an intended orientation.

In a particular embodiment of the method, the end face of the assembly tool and/or an end face of the auxiliary tool bear on the nozzle channel during the continued engagement of the nozzle plate arrangement in the latter. When both end faces are in contact, the position of the nozzle plate arrangement in the nozzle channel can be precisely controlled.

Moreover, by designing the end faces of the assembly tool and/or of the auxiliary tool with a non-planar shape, a deformation of the nozzle plate arrangement can be brought about. In particular, the end face of the assembly tool can have a convexly curved shape, and the end face of the auxiliary tool can have a concavely curved end face. During the insertion of the assembly tool into the nozzle channel, the end faces shaped in this way press the nozzle plate arrangement elastically and/or plastically into a curved shape.

Such a curved shape affords the advantage that the previously parallel nozzle openings are angled with respect to one another and in particular are oriented in a diverging manner. This is advantageous in many applications, since it produces a more fanned-out spray jet.

Moreover, an elastic deformation of the nozzle plate, brought about by the assembly tool and/or the auxiliary tool and in particular by the two tools together, leads to the diameter of the nozzle plate arrangement being temporarily reduced such that the nozzle plate arrangement, in the case of a tapering nozzle channel, can move deeper into the latter. As soon as the force applied to the nozzle plate by the assembly tool and/or the auxiliary tool is withdrawn, there is a particularly strong deformation of a surrounding annular region and thus a high positional stability of the nozzle plate arrangement.

On account of the usually occurring elastic deformation of an annular region surrounding the nozzle plate arrangement and on account of the construction of the individual components, which are also explained in more detail below, without thermal aftertreatment, the method according to the invention leads to a high level of leaktightness and positional stability of the nozzle plate arrangement. However, it can be advantageous if the nozzle plate arrangement, after reaching its end position and after removal of the assembly tool, is heated to the softening temperature of the plastic of the plastic carrier and in particular to at least 100° C., such that the leaktightness in the edge region of the nozzle plate arrangement is further improved. However, this heating preferably does not take place to an extent that would result in a complete loss of the elastic deformation in the stated annular region. The heating can be effected, for example, by means of a laser or by induction.

In the context of producing a nozzle unit, the second of the methods mentioned at the outset is used to attach a flat filter to the plastic carrier of a nozzle unit. The method preferably takes place using a plastic carrier in whose nozzle channel a nozzle plate arrangement has already been fitted, particularly preferably by means of the first method already described.

The stated filter serves the purpose of ensuring that solid constituents from the liquid to be discharged do not reach the nozzle plate arrangement, so as to prevent the nozzle openings from becoming blocked. Just as in the method described above for introducing the nozzle plate arrangement, another aspect of the invention also relates, in connection with the method for attaching the filter, to a nozzle unit having the properties that result from the method.

In the context of the attachment method, a planar filter material is positioned as starting material on the end face of the plastic carrier in a preparatory method step. Only after this positioning does a separation process take place, by which the filter material is cut circumferentially around the end face, such that the flat filter, positioned on the end face and cut circumferentially in situ, remains.

This procedure effectively avoids a situation where contaminants occurring in the course of the separation process get into the nozzle channel. It is not necessary to change the positioning of the filter after the separation process. The risks of contamination associated with this are eliminated. Such contamination is completely avoided especially if, before the separation, the filter material has already been connected to the plastic carrier, in particular by means of a welded connection.

The separating process can be carried out using a mechanical tool such as a cutting edge. Alternatively, however, other separation methods can also be used, for example laser cutting and water jet cutting.

A flat filter within the meaning of the invention is understood to be a planar filter whose thickness is at least a factor of 5 smaller than its diameter. In principle, such a filter can also be in the form of a depth filter, i.e. a filter which, by means of a porous structure, retains contaminants in its interior. However, the use of a membrane filter is particularly preferred, that is to say a filter which has pores of a defined size and which retains contaminants on its surface. In contrast to a depth filter, the pores of such a membrane filter have a defined pore size, generated for example by means of a laser or an electron beam.

The separation limit of such a filter defines the size of particles that are filtered out by at least 99.9% from the liquid and accordingly do not reach the nozzle plate arrangement. The filter is preferably designed to filter at least 99.999% of the particles from the liquid which, in terms of their size, could pose a danger to the nozzle openings by closing the nozzle openings.

The method is particularly advantageous if it is carried out jointly for a plurality of nozzle units. This means that, in the preparatory method step, a continuous planar portion of the filter material is positioned on the end faces of a plurality of plastic carriers of the nozzle units and is preferably thermally attached directly here. In the case of such thermal attachment, a large number of plastic carriers are thus jointly attached to the common portion of the filter material after the preparatory method step.

In the later method step, the separation process then takes place, by means of which the filter material is cut circumferentially around the end faces, such that the flat filters positioned on the end faces, and preferably each thermally attached, remain on the end faces.

The stated thermal joining of the filter to the plastic carrier is preferably carried out by means of a laser welding method or by means of a heated stamping die which presses onto the filter material in the joining direction.

The thermal attachment of the filter to the end face of the plastic carrier is not without alternatives. Thus, in addition or as an alternative, it is also possible for a clamping element, preferably in the manner of a clamping ring, to be connected to the plastic carrier after the separation process, such that the flat filter is held clamped between the end face of the plastic carrier and the clamping element. This clamping connection, which can be configured for example as a radial or axial clamping connection, is explained in more detail below in connection with the nozzle unit itself.

In addition to the stated methods for inserting the nozzle arrangement into the nozzle channel and for positioning and in particular attaching the filter on the plastic carrier, one aspect of the invention also relates to a nozzle unit which is produced in particular by the method steps of the stated methods.

Such a nozzle unit has, according to the method product of the first method mentioned, a plastic carrier which is traversed by a nozzle channel from an inlet side to an outlet side. The plastic carrier preferably has an outer shape which is coaxially rotationally symmetrical with respect to the nozzle channel, so as to be easy to handle during assembly in a liquid dispenser.

A nozzle plate arrangement is arranged in the nozzle channel of the nozzle unit. The nozzle plate arrangement has a multiplicity of nozzle openings, preferably at least 10, particularly preferably at least 30. The average diameter of these nozzle openings is preferably between 1 µm and 100 µm, particularly preferably between 2 µm and 10 µm. In the case of non-round nozzle openings, this diameter information relates to imaginary round nozzle openings with a clear cross section that is equal in size to the non-round nozzle openings.

The nozzle plate arrangement is inserted into the plastic carrier with elastic deformation of the latter, such that at least one annular region of the plastic carrier surrounding the nozzle plate arrangement is in an elastically compressed state and thereby permits secure and tight fastening of the nozzle plate arrangement.

In a preferred embodiment, the nozzle plate arrangement is configured in one piece, in particular in the form of a flat nozzle plate of substantially constant thickness. The nozzle openings are provided in this nozzle plate. The outer contour of this nozzle plate acts on the compressed annular region of the plastic carrier and thereby deforms it. The nozzle plate preferably has an edge region in which the thickness of the nozzle plate tapers in order to act with a particularly narrow ridge on the annular region and thereby penetrate into the inner surface of the annular region. This ensures a very good hold. Despite the penetration, an elastic compression of the annular region remains, which ensures leaktightness in the long term and thus counteracts deterioration of the spray pattern or penetration of contaminants, even during long storage times.

In addition to the one-piece design described, other designs of the nozzle plate arrangement may also be expedient, depending on the intended application and the type of assembly. These include, in particular, a design of the nozzle plate arrangement with a flat nozzle plate and in addition with a carrier frame mounted thereon. The carrier frame has a central aperture, which leaves the nozzle openings of the nozzle plate free. The carrier frame can itself be that part of the nozzle plate arrangement which applies an outward radial force to the annular region. Preferably, however, even with the presence of a carrier frame, it is exclusively (or at least predominantly) the nozzle plate which acts with its preferably thin-walled outer contour directly on the annular region. In this case, the carrier frame therefore has an outer contour which is sufficiently small that the outer contour of the nozzle plate can elastically deform the annular region.

The carrier frame can facilitate the handling of nozzle plate arrangements in advance of the assembly and also facilitate the assembly itself. By being attached in the upstream direction to the nozzle plate, it can in particular serve the purpose of absorbing the force that is coupled directly into the nozzle plate by the described assembly tool.

If a carrier frame is provided, it is preferably made of plastic. The nozzle plate is preferably made of a metallic material, preferably of nickel. The additive manufacturing process of "electroforming" is especially suitable as a manufacturing process. Here, these nozzle openings can already be created in a one-step method. Alternatively, nozzle openings can also be created subsequently by laser. In addition to metallic nozzle plates, it is also possible to use nozzle plates made from other materials, for example silicon nozzle plates.

In the simplest case, the nozzle plate has sufficient inherent stability to remain flat even under the effect of the force generated by the annular region. However, a design may also be advantageous in which the nozzle plate has a curved shape. This curved shape can be generated by plastic deformation, especially in the course of the above-described assembly method or even before assembly. However, depending on the type of material used for the nozzle plate, the curved shape can also be produced by elastic deformation and a residual stress state.

The nozzle channel preferably has a rotationally symmetrical shape. The nozzle plate arrangement also preferably has a round outer contour, since this simplifies assembly and promotes a tight connection to the annular region.

At its end pointing in the direction of the inlet side, the nozzle channel preferably has a clear cross section which is larger than the outer contour of the nozzle plate arrangement. This makes assembly considerably easier. In addition, the large cross section, or a depression surrounding the nozzle channel, is advantageous for the provision of an upstream filter, as is explained further below.

For the purpose of easy assembly, the nozzle channel preferably has a tapering shape. Particularly preferably, the nozzle channel has at least one conical sub-portion with an opening angle of between 5° and 15°. A conical sub-portion with this slope is highly suitable for assembly by means of the assembly tool described above.

The nozzle channel preferably has a plurality of sub-portions, which are each of conical shape but have different opening angles. In particular, in addition to the abovementioned sub-portion with an opening angle of between 5° and 15°, there is a further sub-portion with a larger opening angle. The end position of the nozzle plate arrangement is preferably situated in this region. The larger opening angle improves the accuracy of compliance with an intended end position of the nozzle plate arrangement, that is to say its installation position, and the reproducibility of this end position in mass production.

Downstream from the nozzle plate arrangement, the nozzle channel preferably tapers further, such that the nozzle plate arrangement is followed by an inwardly pointing holding region of the nozzle channel, the clear cross sectional diameter of which holding region is at least 10% smaller than the diameter of the nozzle plate arrangement. In a preferred embodiment, the outer contour of the nozzle plate arrangement is held peripherally by a holding region that is tapered to this extent with respect to the outer contour. The holding region secures the nozzle plate arrangement such that, during assembly or production handling and also during use, it is ensured that the nozzle plate arrangement cannot be forced out of the nozzle channel in the direction of flow, even under particular mechanical loading such as liquid pressure peaks.

In order to achieve a connection between the nozzle plate arrangement and the plastic carrier that is particularly advantageous in terms of stability and leaktightness in the edge region, the plastic carrier, in the deformed annular region surrounding the nozzle plate in its end position, is formed by a wall which surrounds the nozzle channel like a tube and whose wall thickness, in the non-deformed state, is at least in part between 10% and 80% of the clear width of the nozzle channel on the nozzle plate, preferably between 20% and 40%. The outer diameter of the tubular nozzle channel wall is preferably between 3 mm and 15 mm. The wall thickness is preferably between 10% and 30% of this outer diameter.

In accordance with the method product of the second method mentioned above, that is to say the method for positioning or mounting the filter, a nozzle unit has a plastic carrier which is traversed by the nozzle channel and which, on the inlet side of the nozzle channel, has an end face that annularly surrounds the nozzle channel. A flat filter rests on this end face, such that it filters liquid as the latter enters the nozzle channel.

This flat filter is fastened to the plastic carrier and is arranged in such a way that the liquid is filtered even before entering the nozzle channel. The filtering of the incoming liquid serves in particular to remove particles in the liquid that could close the nozzle openings of a nozzle plate in the nozzle channel, in particular a nozzle plate of the type described above, which is inserted with clamping into the nozzle channel.

The filter is attached to the plastic carrier in a leaktight manner all the way round. It is particularly preferable here that the filter is thermally attached to the end face of the plastic carrier to surround the inlet of the nozzle channel. With such a design in particular, it is advantageous, for the thermal attachment, if the end face forms a surface which closes the plastic carrier in the direction of the inlet side and beyond which no other portions of the plastic carrier protrude. The thermal attachment entails a welding process, which is carried out in particular by means of a laser or a hot stamping die.

Alternatively or in addition, the filter can be clamped on the plastic carrier such that it spans the end face of the latter and the inlet of the nozzle channel. Here, an additional clamping element is used, preferably in the manner of a clamping ring, which is connected to the plastic carrier in such a way that the flat filter is held clamped between the clamping element and the plastic carrier. The clamping force can be produced axially, in particular in the region of the end face itself, or radially on the outside of the end face. An inclined orientation of clamping surfaces on the clamping element and on the plastic carrier is also possible.

The filter lies flat on the end face and prevents the penetration of particles into the nozzle channel that would be liable to close the nozzle openings. The filter is flat and, as a flat filter within the meaning of the invention, has an average diameter that is at least five times greater than its average thickness. As has already been described in the context of the method, such a filter can be designed as a depth filter or membrane filter. In the case of a membrane filter, the latter preferably has a support layer that does not take part in the filtration, in particular in the form of a PE nonwoven. This support layer carries the actual filter membrane of the membrane filter.

The separation limit, defined by the particle size, by which up to 99.9% is filtered out, is preferably below the diameter of the nozzle openings of a nozzle plate arrangement inserted into the nozzle channel, preferably at least 40% below the diameter of the nozzle openings. The separation limit of the filter is preferably between 0.5 µm and 100 µm, in particular between 1.5 µm and 10 µm. The filter is preferably designed to filter out from the liquid at least 99.999% of the particles which, in terms of their size, could pose a danger to the nozzle openings by closing said nozzle openings.

The plastic carrier preferably has, on the inlet side, a structure that permits the use of a large filter with a large flow area, which is at least a factor of 2, preferably at least a factor of 3, and particularly preferably at least a factor of 4, larger than the minimum cross-sectional area of the nozzle channel, without taking into consideration a nozzle plate arrangement inserted therein. This structure forms a depression in the end face and is completely covered by the filter. The depression is preferably interrupted by a support structure, such that the filter is supported in some parts and, during the handling of the nozzle unit prior to installation in a liquid dispenser, is not damaged by application of an external force. The support structure can in particular be designed in the form of a multiplicity of support ribs, particularly preferably in the form of support ribs extending inward from an outer edge.

The stated plastic carrier of a nozzle unit according to the invention, which has a nozzle plate arrangement and/or a filter of the type described, is particularly preferably made of PET.

A nozzle unit of the type described is intended to be used in a liquid dispenser. Such a liquid dispenser can be designed principally for the discharge of cosmetic or pharmaceutical liquids. In the case of pharmaceutical liquids, the latter can in particular be ones that are inhaled and for this purpose are atomized by means of the nozzle unit.

The liquid dispenser usually has a liquid reservoir and a housing, into which the nozzle unit of the type described is inserted such that the liquid conveyed from the liquid reservoir is discharged through the nozzle unit.

The liquid dispenser is preferably a small portable liquid dispenser with a liquid reservoir whose maximum volume is between 10 ml and 1000 ml, preferably between 50 ml and 250 ml.

The conveying of liquid from the liquid reservoir to the nozzle unit can be effected, for example, via a preferably manually actuatable pump device. Alternatively, the liquid reservoir can be designed as a pressure reservoir in which the liquid is stored under pressure.

BRIEF DESCRIPTION OF THE DRAWINGS

Further advantages and aspects of the invention will become clear from the claims and from the following description of preferred illustrative embodiments of the invention, which are explained below with reference to the figures.

DETAILED DESCRIPTION OF THE ILLUSTRATIVE EMBODIMENTS

Figure 1:
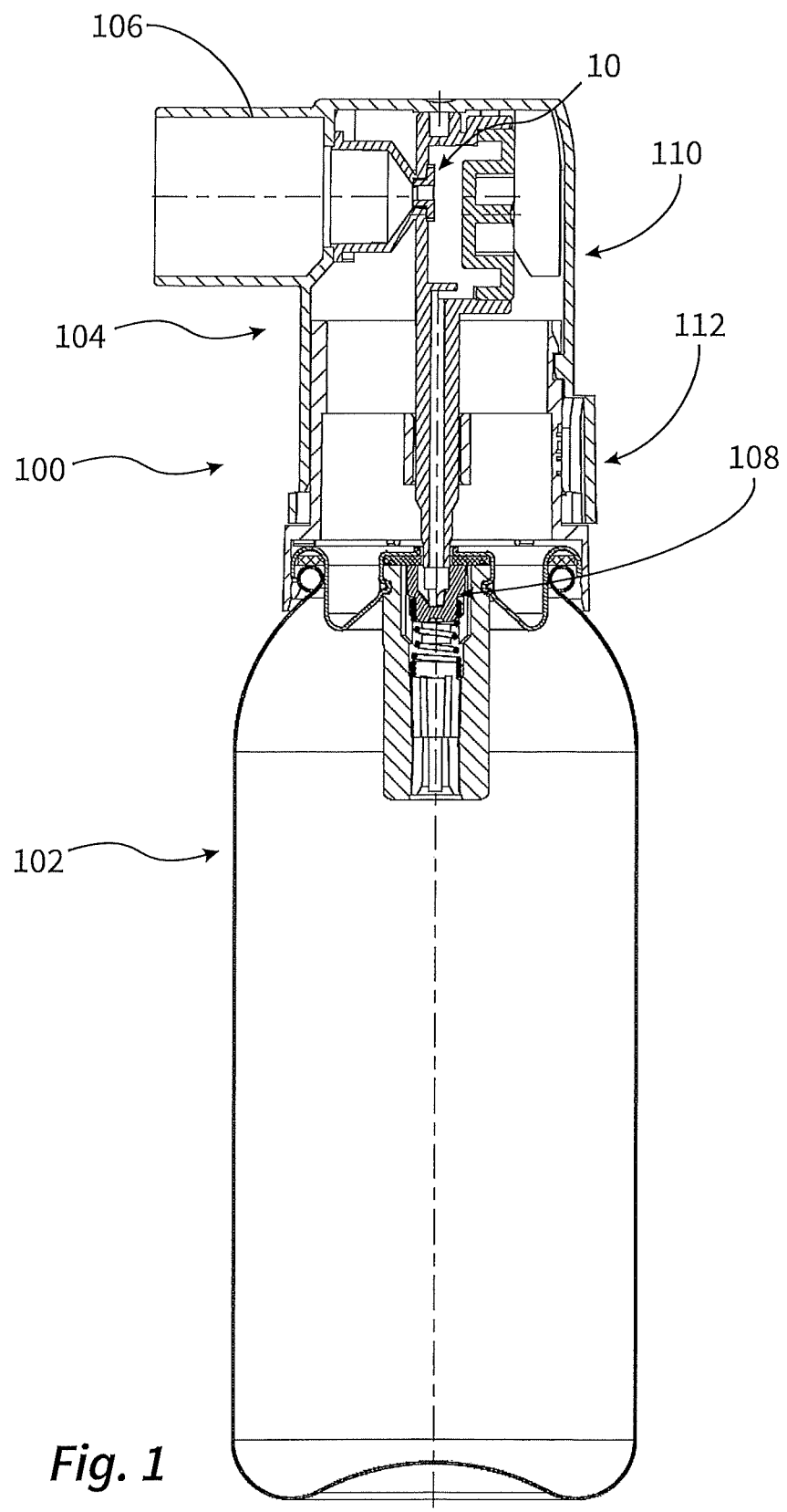
FIG. 1 shows a liquid dispenser, which exemplifies a typical use of a nozzle unit according to the invention.

FIG. 1 shows a liquid dispenser 100 having a nozzle unit 10 according to the invention. This liquid dispenser 100 is to be understood as an exemplary liquid dispenser for a nozzle unit 10. Many other designs of liquid dispensers using nozzle units 10 according to the invention are also conceivable.

The liquid dispenser 100 of FIG. 1 has a pressure reservoir 102 in which liquid is stored before being discharged. A discharge head with a housing 104 is mounted on this pressure reservoir 102. This discharge head has a base 112, and an actuation button 110 that can be depressed relative to the latter. When this actuation button 110 is depressed, it acts on an outlet valve 108 of the pressure reservoir 102 such that liquid flows into the discharge head and reaches the nozzle unit 10. An outlet piece 106, in the present case taking the form of a mouthpiece 106 for example, is provided downstream from the nozzle unit 10. By means of the nozzle unit 10, the inflowing liquid is brought into the form of a spray jet, which is dispensed into the outlet piece 106 and can be inhaled by a user.

FIGS. 2 to 4 and 4A to 4D first illustrate, on the basis of a first illustrative embodiment and variants, the structure of a nozzle unit 10 according to the invention.

Figure 2:
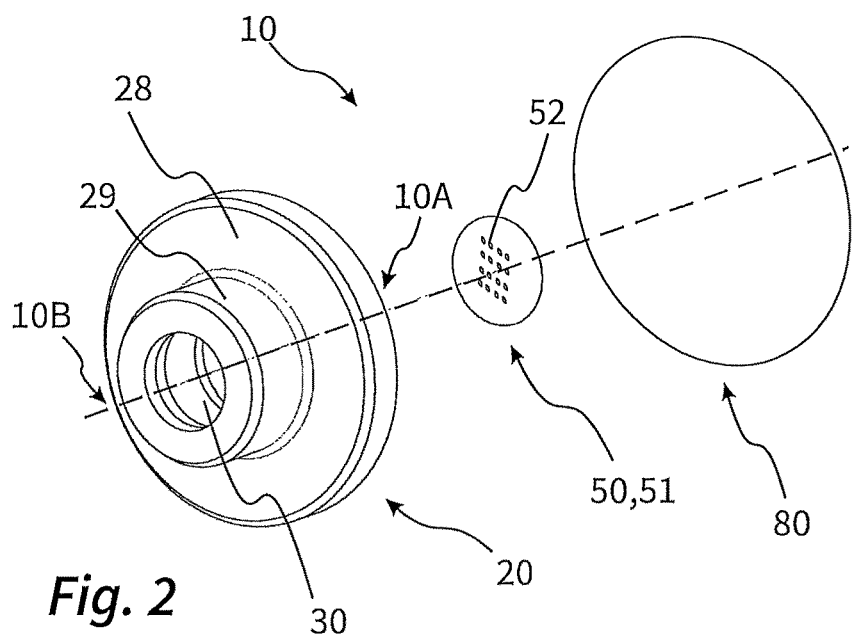
FIGS. 2 to 4 show, in an exploded view, a parts view and a sectional view, a first illustrative embodiment of a nozzle unit according to the invention and parts thereof.

FIG. 2 shows the individual components in an exploded view.

As its load-bearing component, the nozzle unit 10 has a plastic carrier 20 which has approximately the shape of a top hat with a brim portion 28 and a cylinder portion 29. The plastic carrier is traversed by a nozzle channel 30 from an inlet side 10A to an outlet side 10B.

A nozzle plate arrangement 50 and a filter 80 are inserted or attached from an inlet side 10A. In the illustrative embodiment of FIGS. 2 to 4, the nozzle plate arrangement 50 is formed solely by a thin nozzle plate 51. In this nozzle plate 51, a multiplicity of nozzle openings 52 are provided in a matrix-like arrangement. In a manner explained in more detail below, the filter 80 is applied to an end face 20A of the plastic carrier 20 pointing in the direction of the inlet side 10A.

Figure 3:
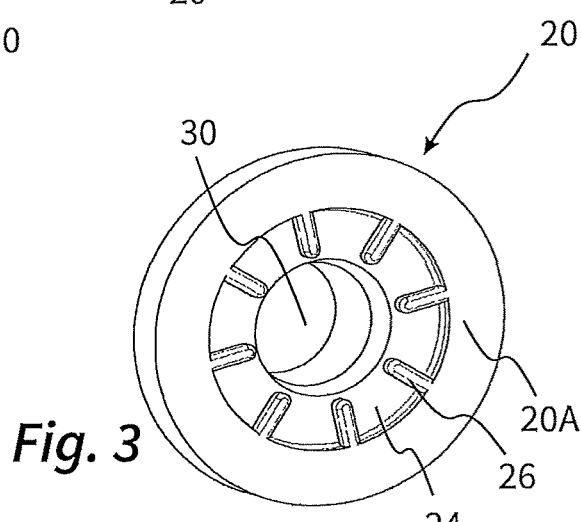

FIG. 3 shows the plastic carrier 20 from the opposite side, that is to say the inlet side 10A of the plastic carrier 20. It will be seen here that, on the inside of the circumferential end face 20A, a depression 24 is provided which surrounds the nozzle channel 30 and into which support ribs 26 protrude from the outside.

Figure 4:
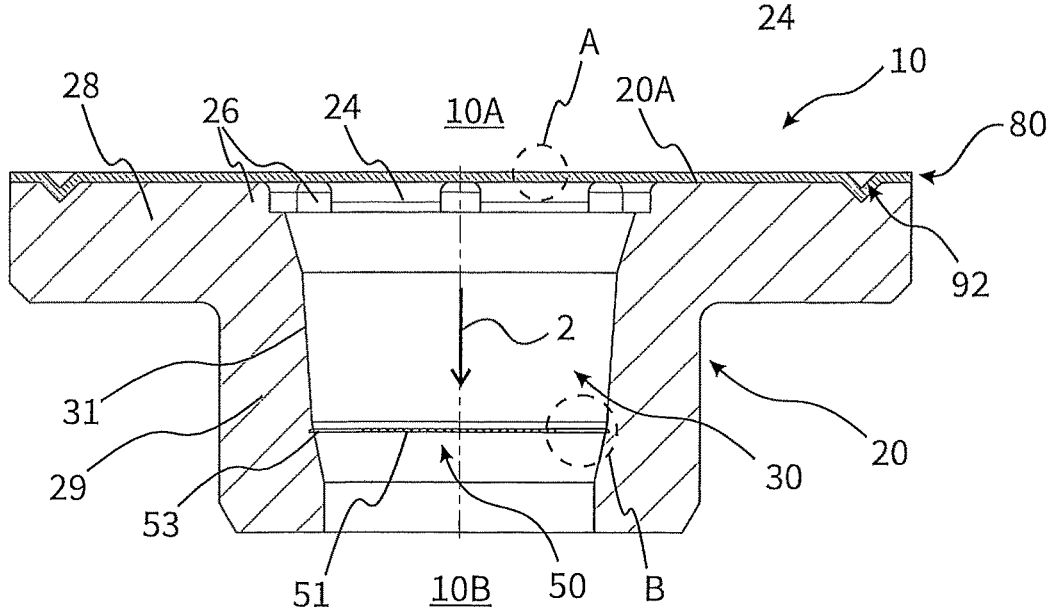

Referring to FIG. 4, the structure of the nozzle unit 10 can be seen in the assembled state. It will be seen that the nozzle plate 51 has penetrated with its edge region 53 into a nozzle channel wall 31 and is thereby fixed. It will also be seen that the nozzle channel 30 has a shape tapering as a whole in the joining direction 2, with various conical sub-portions being provided.

The filter 80 is positioned on the end face 20A and is welded to the plastic carrier 20 in the region of a circumferential welding point 92. On account of the depression 24, the effective surface area of the filter 80 is very large, in the present case approximately twice as large as the cross section of the nozzle channel 30 at the narrowest point thereof. As a result, the filter 80 can filter comparatively large quantities of liquid without clogging.

The filter 80 can, for example, have a separation limit of 4 μm, i.e. can filter out all or almost all of the particles that cannot pass the filter in the case of pores of corresponding size. The stated separation limit of 4 μm is very suitable if the nozzle openings 52 have a clear or open cross section of 8 μm. This coordination ensures that all constituent parts of the liquid that can pass through the filter 80 can also be dispensed through the nozzle openings.

Figure 4A:
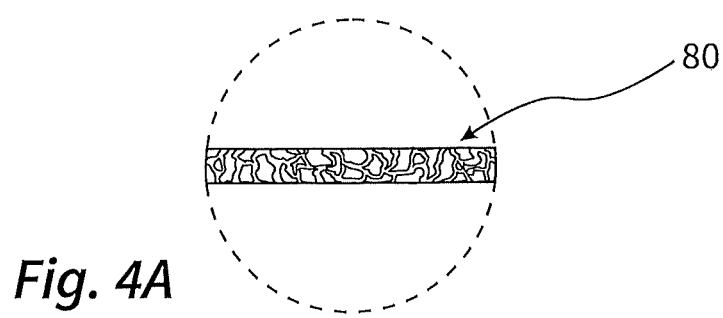
FIGS. 4A to 4D show details and detail variants of FIG. 4.
Figure 4B:
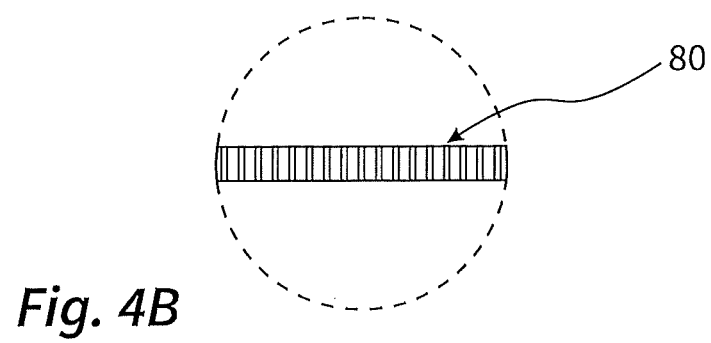
Figure 4C:
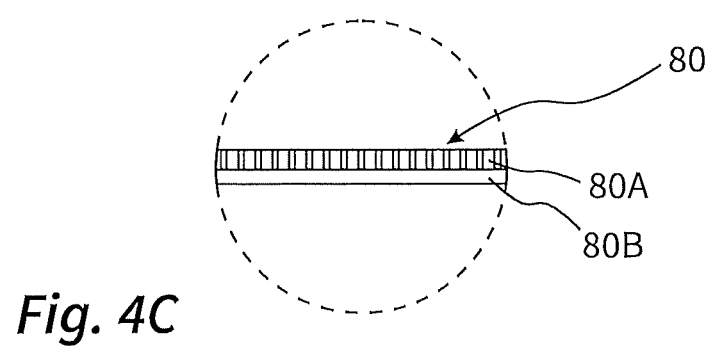

As is shown in FIGS. 4A to 4C, the filter 80 can be designed in various ways. FIGS. 4A to 4C show variants of the region A indicated in FIG. 4.

In the design according to FIG. 4A, a depth filter is used, i.e. a filter 80 made of a porous and, for example, sintered material which is penetrated by irregular pores, the effect of which is that particles of a certain size cannot penetrate the depth filter, but instead are retained therein.

FIG. 4B shows a design with a membrane filter as filter 80. This has filter openings 82 which have a defined position and shape and which may have been introduced into filter 80 or its filter material 180 by means of a laser beam, for example. Particles that are larger than the cross section of these filter openings cannot penetrate the filter 80 and collect on the upstream side of the filter 80.

FIG. 4C shows a variant in which a membrane filter is likewise used as filter 80. This has a filter membrane 80A similar to that of FIG. 4B. In addition, a carrier layer 80B made of a coarse nonwoven is provided, which gives the filter membrane 80A the necessary stability.

Figure 4D:
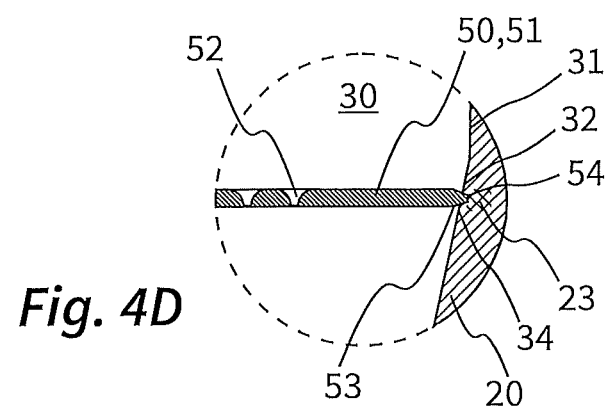

FIG. 4D shows the region B of FIG. 4, in which the nozzle plate 51 bears on the nozzle channel wall 31. It will be seen that the nozzle plate 51 penetrated by nozzle openings 52 has a tapering shape in the edge region 53 and that the outer contour 54 of the nozzle plate 51, on account of the assembly method described below, leads to a compression zone 23 being formed in the region of the nozzle channel wall 31, in which compression zone 23 the plastic material of the plastic carrier 20 is compressed. Downstream and upstream from the nozzle plate 51, the nozzle channel wall 31 projects inward beyond the edge region 53 of the nozzle plate 51, such that the nozzle plate 51 is secured with a form-fit engagement.

FIGS. 5A to 5G show the method for introducing the nozzle plate 51 into the plastic carrier 20.

Figure 5A:
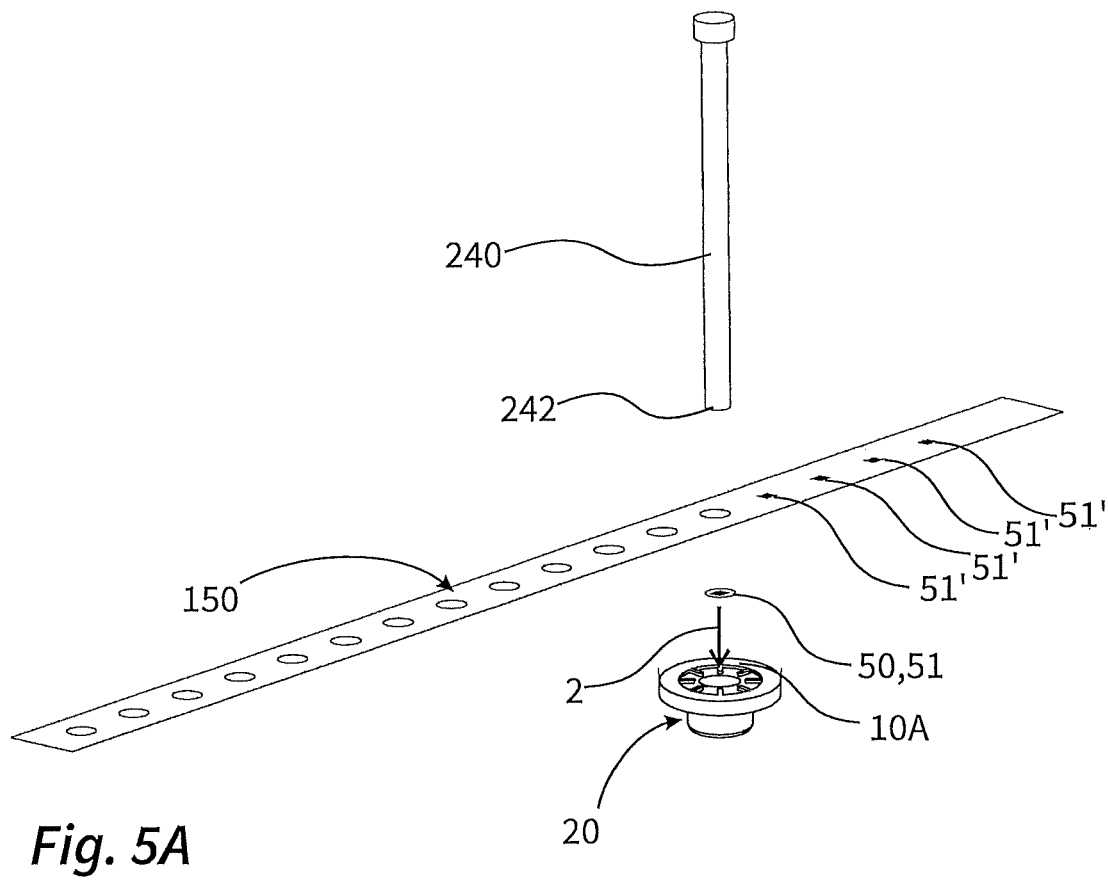
FIGS. 5A to 5G show a first sub-method for producing the nozzle unit of FIGS. 2 to 4, in the context of which a nozzle plate arrangement is inserted into the nozzle channel of the nozzle unit.

As is shown in FIG. 5A, starting from a carrier plate 150 having a multiplicity of nozzle plate regions 51' with nozzle openings 52, a nozzle plate 51 is first of all punched out by means of a punching tool 240 and its end-face punching surface 242, which nozzle plate 51, in the present configuration, alone forms the nozzle plate arrangement 50. This nozzle plate 51 is inserted into the plastic carrier 20 from the inlet side 10A, in the joining direction 2, immediately after the punching operation, i.e. without intermediate storage with other nozzle plates.

Figure 5B:
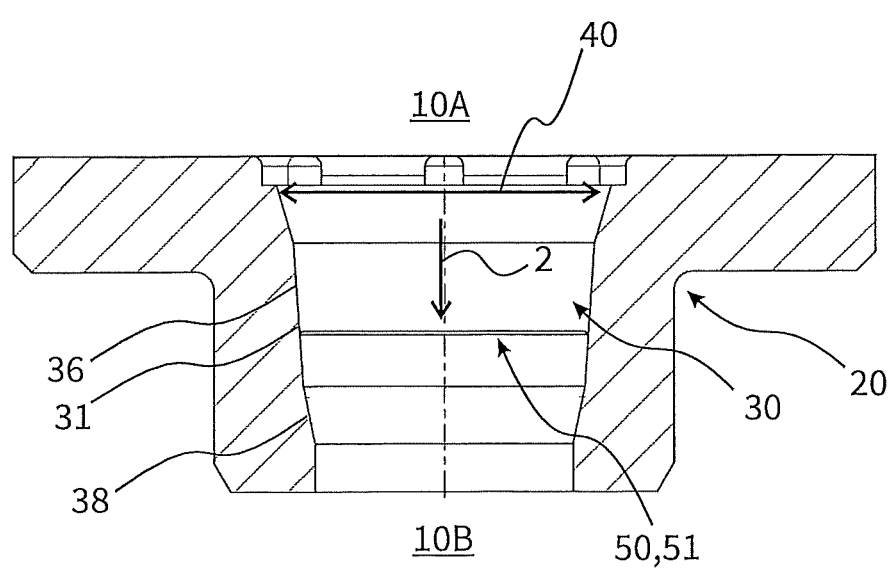

As will be seen from FIG. 5B, on account of the inlet side 10A having a cross section 40 larger than the outer contour 54 of the nozzle plate 51, said nozzle plate 51 immediately reaches quite deep into the nozzle channel 30 and first comes to lie in a conical sub-portion 36 of the nozzle channel wall 31.

Figure 5C:
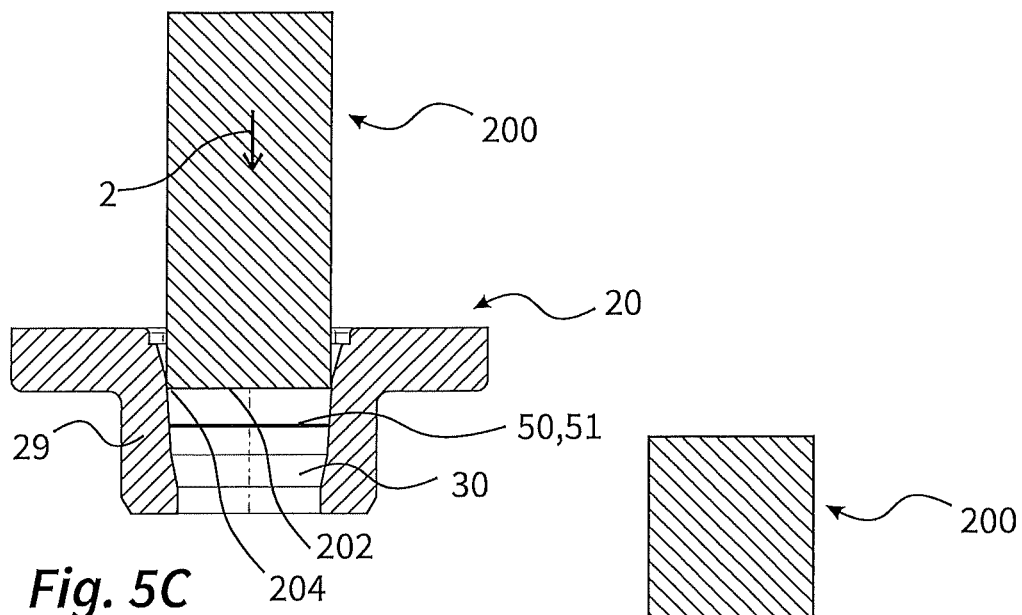
Figure 5D:
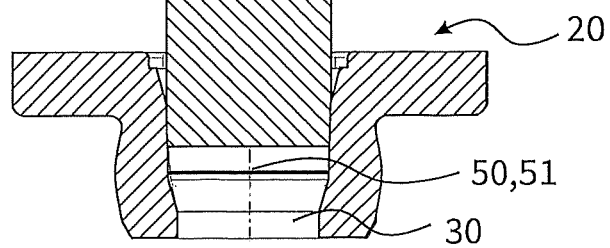

As is illustrated in FIG. 5C, an assembly tool 200 is then pushed into the nozzle channel 30 from above in the joining direction 2. With its outer contour 202, the assembly tool 200 likewise comes into contact with the nozzle channel wall 31 in the conical sub-portion 36. In the course of the continued movement of the assembly tool 200 in the joining direction 2, said assembly tool 200, as can be seen in FIG. 5D, begins to elastically expand the nozzle channel 30.

Figure 5E:
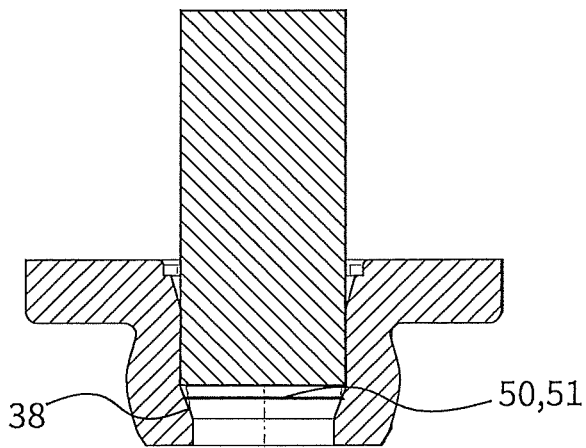

As a result of this expansion, the nozzle plate 51 also sinks increasingly downward in the joining direction, until it reaches its end position, shown in FIG. 5E, in a second conical sub-portion 38. In the present example, this further movement of the nozzle plate 51 does not require any direct contact with the assembly tool 200. However, in other configurations of the method, provision may also be made that the assembly tool 200 is in contact with the nozzle plate 51 and is thereby able to push the latter deeper into the nozzle channel 30.

Figure 5F:
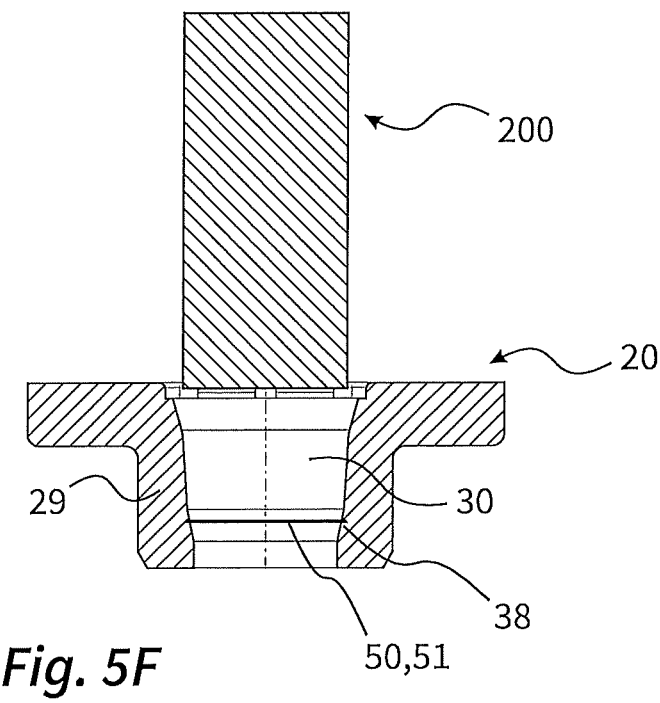
Figure 5G:
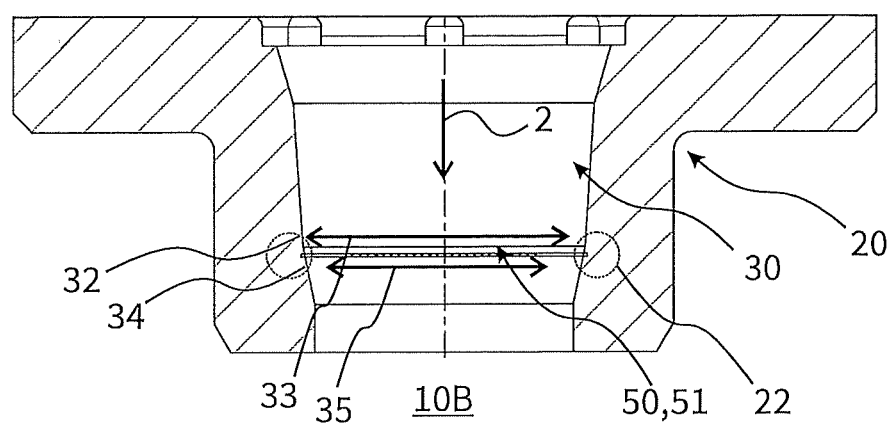

Finally, in the manner illustrated in FIG. 5F, the assembly tool 200 is pulled out of the nozzle channel 30 counter to the joining direction 2. The nozzle plate 51 remains in the nozzle channel 30. The nozzle channel wall 31, which in the meantime has expanded elastically, returns to its starting position, although, on account of the nozzle plate 51, it cannot completely reset itself in an annular region 22 in the region of the end position of the nozzle plate 51, such that the compression zone 23 already mentioned, which is shown in FIG. 4D, remains in a circumferential annular region 22. On both sides of this compression zone 23 in the region of nozzle channel portions 32, 34, however, the nozzle channel wall 31 is reset. The nozzle channel wall 31 returns to its initial position to such an extent that the cross sections 33, 35 there are smaller than the outer contour 54 of the nozzle plate 51.

The assembly method described leads to secure attachment of the nozzle plate 51 in the nozzle channel 30. Even external forces during assembly, and pressure peaks during operation, cannot loosen the nozzle plate 51. The remaining elastic compression in the compression zone 23 ensures that the nozzle plate 51 is held securely even in the case of lengthy storage times.

Figure 6A:
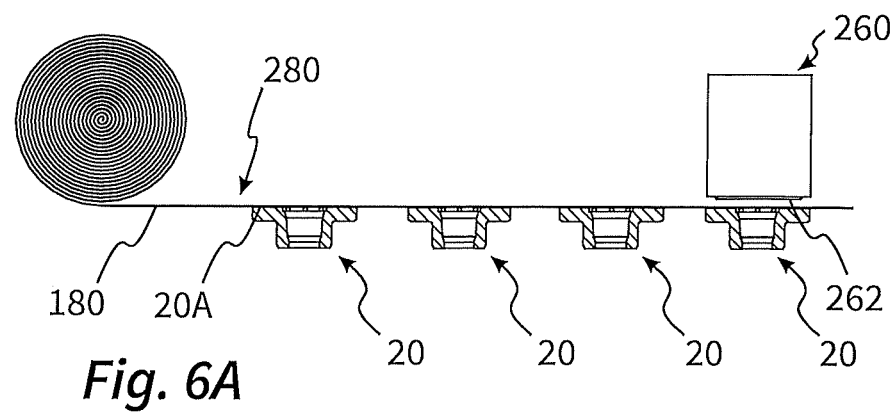
FIGS. 6A to 6C illustrate a second sub-method for producing the nozzle unit of FIGS. 2 to 4, in the context of which a filter is mounted on the nozzle unit.
Figure 6B:
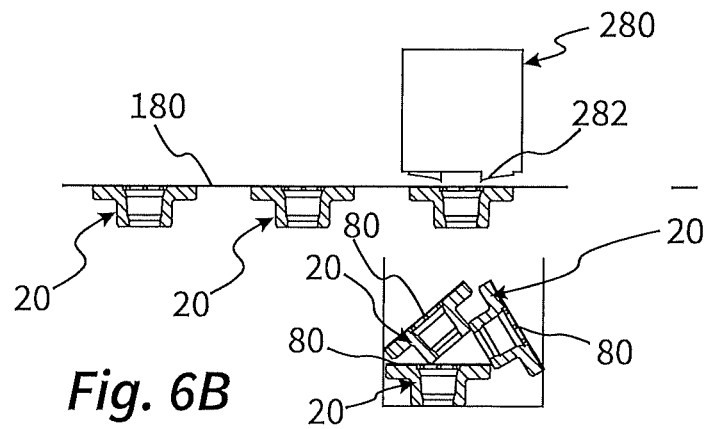
Figure 6C:
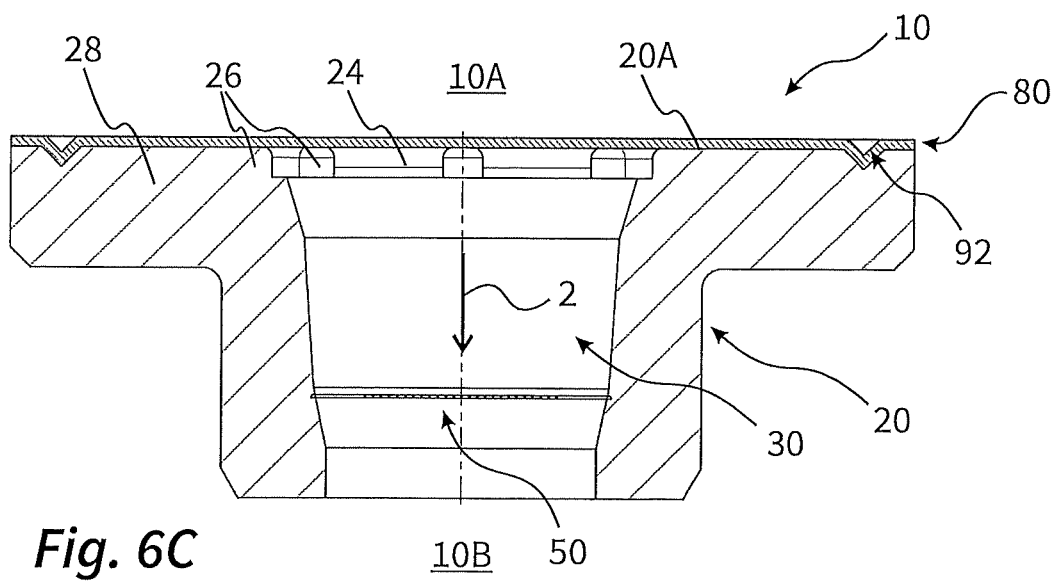

FIGS. 6A to 6C illustrate the application of the filter 80, wherein the method is preferably carried out with nozzle units 10 which are not yet finished and which have been mounted in accordance with the description of FIGS. 5A to 5G.

Referring to FIG. 6A, it will be seen that a filter material 180 is used which can be unwound from a roll, for example. This filter material 180 is placed over the plastic carrier 20 already provided with the nozzle plate arrangement 50, such that, preferably in the context of a continuous process, the plastic carrier 20 is subsequently welded to the filter material 180 by means of a joining stamp 260 and by means of a circumferential joining edge 262 provided therein.

A portion of the filter material 180 is thus obtained on which a large number of plastic carriers 20 with nozzle plate arrangements 50 are thermally fastened. Proceeding from this, in the manner illustrated by FIG. 6B, the filter material 180 is cut all around the end face 20A by means of a cutting tool 280 with a cutting face 282. The nozzle units 10 thus finished, but not yet mounted, can be easily handled in the manner indicated in FIG. 6B. By virtue of the already applied filter 80 and by virtue of the interior of the nozzle units 10 being free from disruptive particles on account of the described production method, and also on account of the secure closure of the nozzle units 10 by the nozzle plates 51, there is no danger of the nozzle units 10 thus finished being contaminated during operation.

FIG. 6C shows once again one of the finished nozzle units 10 with the filter 80 which remains after the cutting process and which is tightly closed in the region of the circumferential welding point 92 by the joining edge 262 of the joining tool 260.

Figure 7:
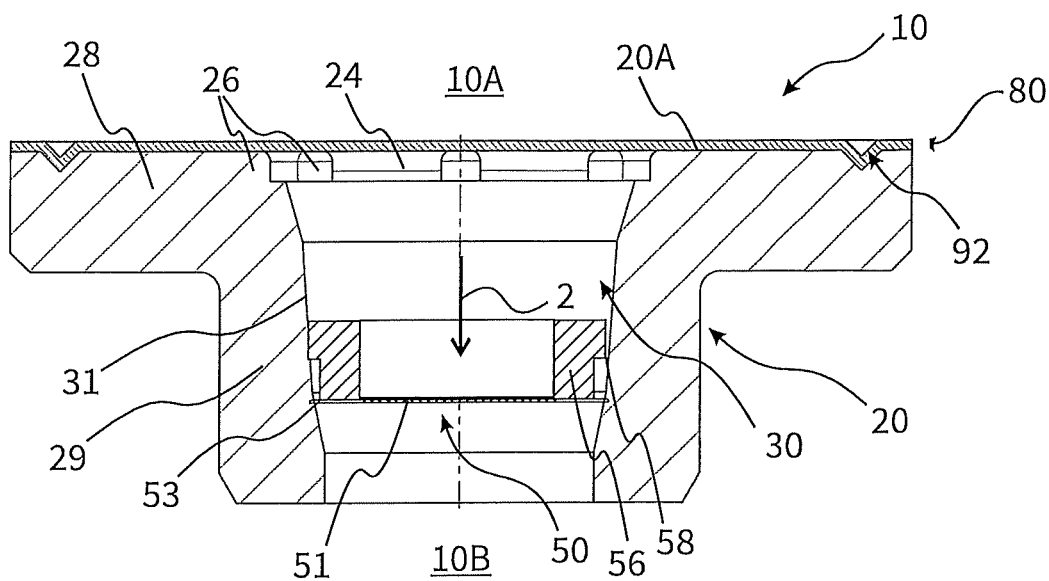
FIGS. 7 and 8 show a second illustrative embodiment of a nozzle unit according to the invention in a sectional view and an exploded view.
Figure 8:
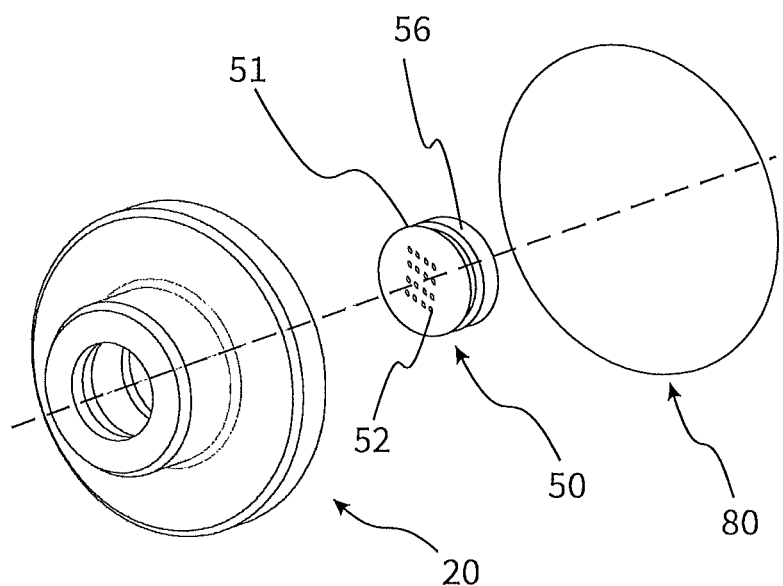

FIGS. 7 and 8 show an alternative design of the nozzle unit 10. A significant difference compared to the nozzle unit 10 of FIG. 4 lies in the design of the nozzle plate arrangement 50. In the present case, this is not only composed of the nozzle plate 51 but additionally comprises a carrier frame 56 made of plastic, which is provided on the upstream side of the nozzle plate 51. The carrier frame 56 can, for example, be injection molded onto the nozzle plate. It has a shape, and in particular an outer contour 58, which allows the edge region 53 of the nozzle plate 51 to be firmly connected to the nozzle channel wall 31 in the manner described. The carrier frame 56 gives the nozzle plate arrangement 50 as a whole a higher intrinsic stability and also reduces the danger of the nozzle plate 51 being damaged by the assembly tool 200 during the assembly process.

Figure 9:
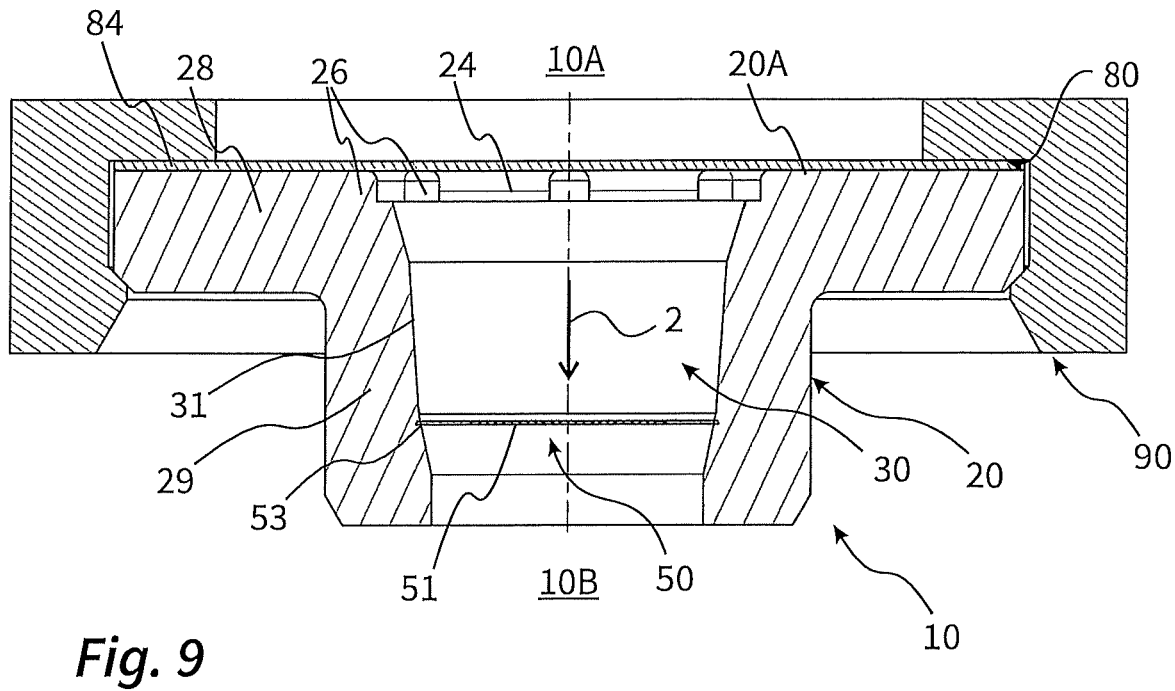
FIGS. 9 to 11 show further illustrative embodiments of a nozzle unit according to the invention, which have an additional clamping element for fastening the filter.

FIG. 9 shows an alternative design, in which a clamping element 90 in the form of a clamping ring 90 is provided, which in the present case is provided instead of the welding point 92. Accordingly, the filter 80 here is not cohesively bonded to the plastic carrier 20, and instead it is pressed axially, in an edge-side clamping region 84, against the end face 20A of the plastic carrier by the clamping ring 90 that encompasses the brim portion 28.

Figure 10:
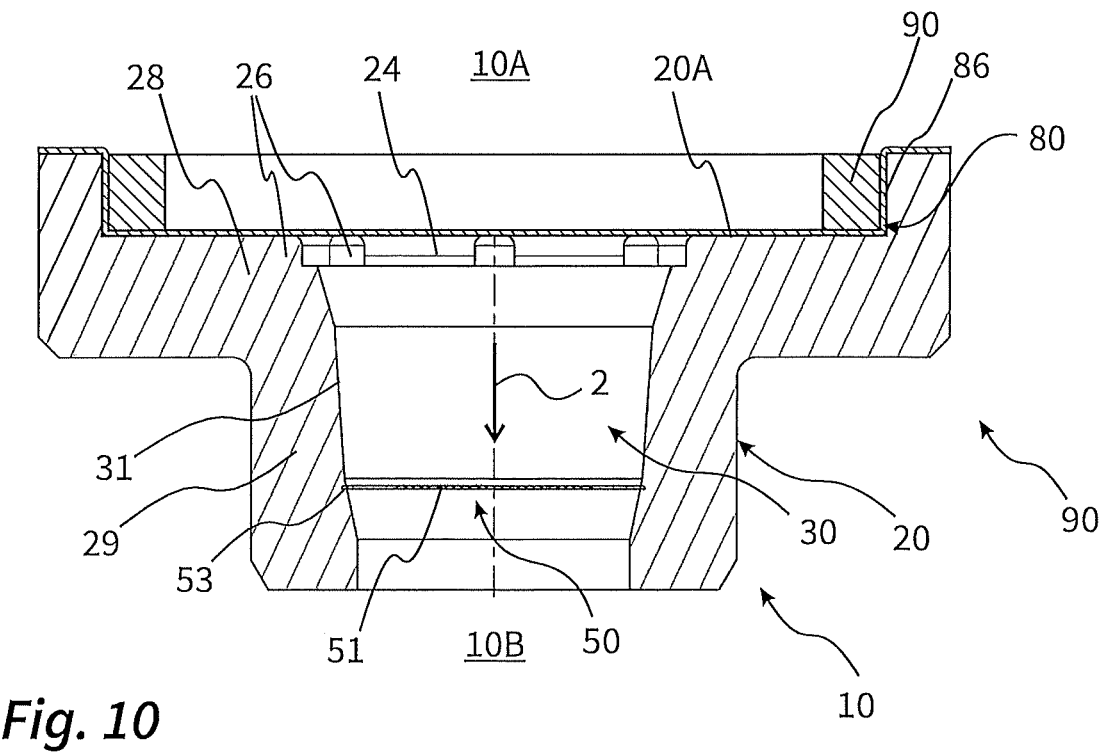

In the design in FIG. 10 also, the flat filter 80 is fixed by a clamping element 90 in the form of a clamping ring 90. Here, however, the clamping ring 90 is pushed into a depression of the plastic carrier 20 and, between its outside and the edge of the depression of the plastic carrier 20, clamps the material of the filter 80 radially in an edge-side clamping region 86.

Figure 11:
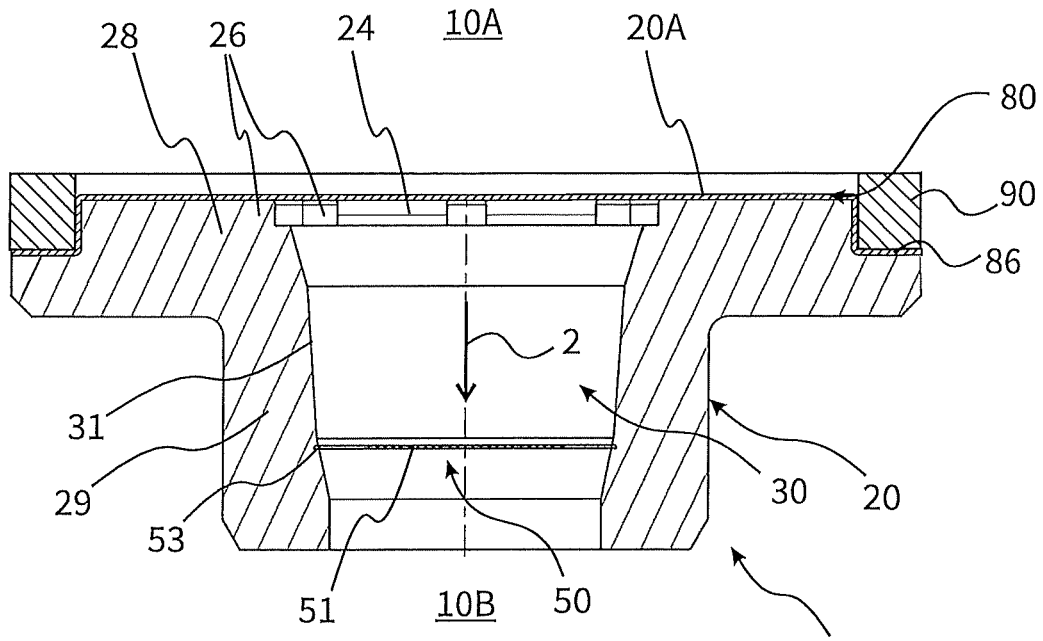

The alternative design in FIG. 11 shows the same basic principle with radial clamping of the filter 80 in the clamping region 86; here, the clamping ring 90 is arranged on the outside of the plastic carrier 20, such that it is an inner surface of the clamping ring 90 which in this case clamps the edge region of the filter 80.

Figure 12:
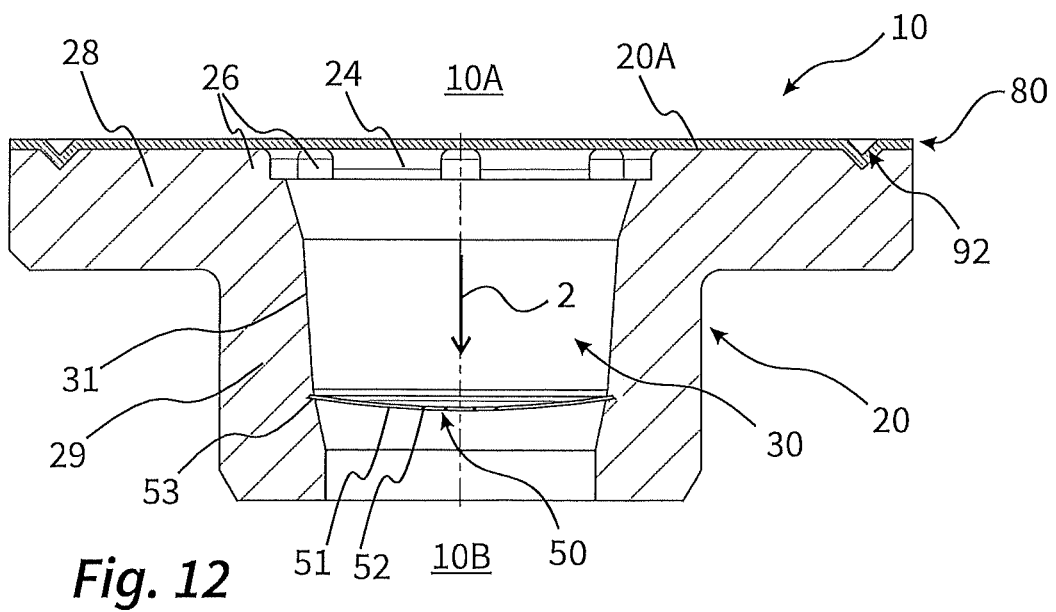
FIGS. 12 and 13 show an illustrative embodiment of the nozzle unit with a curved nozzle plate, and the method for introducing this nozzle plate into the nozzle channel.

FIG. 12 shows an alternative design to that of FIG. 4, which differs from the latter in that the nozzle plate 51 adopts a curved configuration. Such a curved configuration can be advantageous on account of the diverging orientation of the nozzle openings 52 and produces a spray jet that is fanned out to a greater extent.

To produce such a design, it is possible to press the nozzle plates 51 plastically into a curved shape prior to introduction into the nozzle channel 30 and to carry out the method according to FIGS. 5A to 5E otherwise unchanged.

Figure 13:
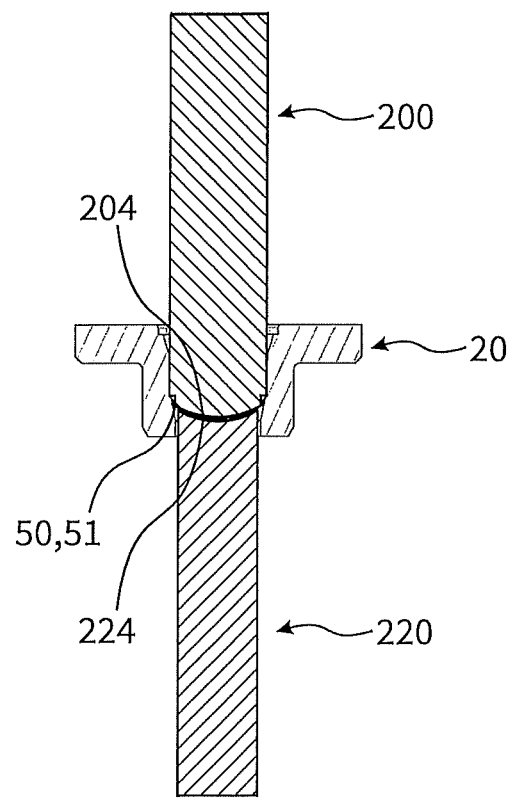

However, as is shown in FIG. 13, provision can alternatively also be made that the assembly tool 200 has a convexly curved end face 204, and an auxiliary tool 220 is pushed into the nozzle channel 30 from the opposite side. This auxiliary tool 220 has a likewise curved, and in this case concavely curved, end face 224. During assembly, the assembly tool 200 and the auxiliary tool 220 together elastically press the originally flat nozzle plate 51 into a curved shape and bring it to its end position in this elastically deformed state. When the assembly tool and the auxiliary tool 220 are then pulled out of the nozzle channel 30 in opposite directions, this curved shape is at least partially retained.

The invention claimed is:

1. A method for producing a nozzle unit for a liquid dispenser, the nozzle unit including a plastic carrier traversed by a nozzle channel from an inlet side to an outlet side, a nozzle channel wall defining the nozzle channel, and a nozzle plate arrangement having a multiplicity of nozzle openings, the method comprising the steps of:
   providing an assembly tool having an outer contour, the outer contour being oversized in relation to the nozzle channel, and an end face larger than an outer contour of the nozzle plate arrangement;
   bringing the plastic carrier into a defined assembly position;
   inserting the nozzle plate arrangement and then the assembly tool in a joining direction into the nozzle channel from the inlet side;
   progressively inserting the assembly tool into the nozzle channel in the joining direction and applying force to the nozzle channel wall with the assembly tool to partially elastically expand the nozzle channel wall outwardly from an initial unexpanded starting position to bring the nozzle plate arrangement to an end position within the nozzle channel at an elastically expanded area of the nozzle channel wall;
   pulling the assembly tool out of the nozzle channel counter to the joining direction and permitting the elastically expanded nozzle channel wall to move back inwardly towards the initial unexpanded starting position, wherein the nozzle plate arrangement remains in the end position at the elastically expanded area of the nozzle channel wall; and
   completely removing the assembly tool from the nozzle channel, thereafter the nozzle plate arrangement being held at the end position by the elastically expanded area of the nozzle channel wall as a result of the movement of the nozzle channel wall back inwardly towards the initial unexpanded starting position.

2. The method as claimed in claim 1, wherein the nozzle plate arrangement is configured as a one-piece nozzle plate, and the method further comprises punching out, by a punching process, the one-piece nozzle plate from a carrier plate with a plurality of nozzle plate regions, and after the one-piece nozzle plate has been punched out, directly inserting the one-piece nozzle plate into the nozzle channel in the joining direction from the inlet side.

3. The method as claimed in claim 1, wherein the nozzle channel has at least one conical sub-portion, the at least one conical sub-portion, at an end thereof pointing in a direction of the inlet side, has a cross section larger than the outer contour of the assembly tool, and, at an end pointing in a direction of the outlet side, the at least one conical sub-portion has a cross section smaller than the outer contour of the assembly tool, and during the step of progressively inserting the assembly tool into the nozzle channel, the assembly tool comes into contact with the nozzle channel wall of the nozzle channel at the at least one conical sub-portion.

4. The method as claimed in claim 1, wherein during the step of progressively inserting the assembly tool into the nozzle channel in the joining direction, an auxiliary tool is inserted, in alignment with the assembly tool, into the nozzle channel from the outlet side.

5. The method as claimed in claim 4, wherein the end face of the assembly tool has a convexly curved shape and/or an end face of the auxiliary tool has a concavely curved end face, and during the step of progressively inserting the assembly tool into the nozzle channel, the concave shape and/or the convex shape presses the nozzle plate arrangement elastically and/or plastically into a curved shape.

6. The method as claimed in claim 1, further including orienting the plastic carrier, in the defined assembly position, so that the inlet side points upward and the outlet side points downward, and after pulling the assembly tool out of the nozzle channel, heating the nozzle plate arrangement, at least in parts, at least up to 100° C.

7. The method as claimed in claim 1, wherein after the step of inserting the nozzle plate arrangement and then the assembly tool in the joining direction into the nozzle channel from the inlet side, the method further includes positioning a planar filter material on an end face of the plastic carrier and thereafter cutting the filter material circumferentially around the end face such that a flat filter remains positioned on the end face of the plastic carrier.

8. A nozzle unit for a liquid dispenser, comprising:
   a plastic carrier having an inlet side, an outlet side, a nozzle channel traversing the plastic carrier from the inlet side to the outlet side, and at least one annular region defining part of the nozzle channel, at least the at least one annular region of the plastic carrier comprising an elastic plastic material; and a nozzle plate arrangement inserted into the nozzle channel between the inlet side and the outlet side and having a multiplicity of nozzle openings, the at least one annular region of the plastic carrier comprising a compressed elastic portion of the elastic plastic material in an elastically compressed state, the compressed elastic portion in the elastically compressed state surrounding the nozzle plate arrangement.

9. The nozzle unit as claimed in claim 8, wherein the nozzle plate arrangement has a shape curved in a direction of the outlet side.

10. The nozzle unit as claimed in claim 8, wherein the nozzle plate arrangement has a round outer contour.

11. The nozzle unit as claimed in claim 8, wherein the nozzle channel has a tapering shape.

12. The nozzle unit as claimed in claim 8, wherein the nozzle plate arrangement comprises a one-piece nozzle plate.

13. The nozzle unit as claimed in claim 8, wherein the nozzle plate arrangement comprises a one-piece nozzle plate having an outer contour and a carrier frame fixed to the one-piece nozzle plate and having a central aperture, the carrier frame being disposed on a side of said one-piece nozzle plate facing said inlet side of said plastic carrier, said carrier frame having an outer contour smaller than the outer contour of the one-piece nozzle plate, the outer contour of the one-piece nozzle plate being firmly fixed in the compressed elastic portion in the elastically compressed state of the at least one annular region of the plastic carrier.

14. The nozzle unit as claimed in claim 13, wherein the outer contour of the one-piece nozzle plate comprises a tapering edge region in contact with the compressed elastic portion in the elastically compressed state of the at least one annular region of the plastic carrier.

15. The nozzle unit as claimed in claim 8, wherein the nozzle channel has, at an end pointing in a direction of the inlet side, a cross section larger than an outer contour of the nozzle plate arrangement, the nozzle plate arrangement comprises a nozzle plate having at least 10 nozzle openings, the nozzle openings have an average diameter of between 1 µm and 100 µm, the plastic carrier, in the at least one annular region, comprises a nozzle channel wall surrounding the nozzle channel and having a wall thickness between 10% and 80% of a width of the nozzle channel, and an outer diameter of the nozzle channel wall is between 3 mm and 15 mm and the wall thickness of the nozzle channel wall is between 10% and 30% of the outer diameter.

16. The nozzle unit as claimed in claim 8, wherein the plastic carrier comprises PET, and the nozzle plate arrangement comprises a metallic material comprising nickel or silicon.

17. The nozzle unit as claimed in claim 8, wherein the plastic carrier has an end face at the inlet side annularly surrounding the nozzle channel, and the nozzle unit further comprises a flat filter disposed on the end face.

18. The nozzle unit as claimed in claim 8, wherein the compressed elastic portion is configured to exert a compressive inward force on the nozzle plate arrangement.

19. A nozzle unit for a liquid dispenser, comprising:
a plastic carrier traversed by a nozzle channel from an inlet side to an outlet side, the plastic carrier having, at the inlet side, an end face annularly surrounding the nozzle channel, the end face defining therein a depression having a surface area being at least a factor of 2 as large as a minimum cross-sectional area of the nozzle channel; and a flat filter for filtering discharged liquid, the flat filter lying on the end face of the plastic carrier.

20. The nozzle unit as claimed in claim 19, wherein the end face and the flat filter together define a surface, the surface closing the plastic carrier at the inlet side and no other portion of the plastic carrier protrudes beyond the surface.

21. The nozzle unit as claimed in claim 19, further comprising a nozzle plate arrangement inserted into the nozzle channel between the inlet side and the outlet side and having a multiplicity of nozzle openings, and the flat filter is configured to filter the liquid before delivery of the liquid to the nozzle plate arrangement.

22. The nozzle unit as claimed in claim 19, further comprising a clamping element connected to the plastic carrier, the flat filter being clamped between the end face of the plastic carrier and the clamping element.

23. The nozzle unit as claimed in claim 19, wherein the flat filter is configured as a self-supporting membrane filter, or the flat filter is configured as a layer composite including a carrier layer of a coarse-pored nonwoven, and a membrane filter, the coarse-pored nonwoven comprising PE, and the membrane filter comprising PET, or the flat filter is configured as a depth filter, or the flat filter has a separation limit of between 0.5 µm and 100 µm.

24. A liquid dispenser for discharging a liquid, comprising:
a liquid reservoir;
a housing; and
a nozzle unit inserted into the housing of the liquid dispenser, the nozzle unit comprising:
a plastic carrier having an inlet side, an outlet side, a nozzle channel traversing the plastic carrier from the inlet side to the outlet side, and at least one annular region, at least the at least one annular region of the plastic carrier comprising an elastic plastic material; and
a nozzle plate arrangement inserted into the nozzle channel between the inlet side and the outlet side and having a multiplicity of nozzle openings, the at least one annular region of the plastic carrier comprising a compressed elastic portion of the elastic plastic material in an elastically compressed state, the compressed elastic portion in the elastically compressed state surrounding the nozzle plate arrangement.

25. The liquid dispenser as claimed in claim 24, comprising at least one of the following:
the liquid reservoir has a maximum volume of between 10 ml and 1000 ml; and/or
the liquid dispenser comprises a manually actuatable pump device, the pump device conveying the liquid from the liquid reservoir to the nozzle unit; and/or
the liquid reservoir comprises a pressure reservoir, the pressure reservoir storing the liquid under pressure, and the liquid comprises cosmetic or pharmaceutical liquid.

26. The liquid dispenser as claimed in claim 24, wherein the compressed elastic portion is configured to exert a compressive inward force on the nozzle plate arrangement.

* * * * *